United States Patent [19]

Davis

[11] 4,303,644

[45] Dec. 1, 1981

[54] FELINE INFECTIOUS PERITONITIS VIRUS VACCINES

[75] Inventor: Eldon Davis, Lincoln, Nebr.

[73] Assignee: Norden Laboratories, Inc., Lincoln, Nebr.

[21] Appl. No.: 85,435

[22] Filed: Oct. 16, 1979

[51] Int. Cl.³ .................. A61K 39/12; A61K 39/215
[52] U.S. Cl. ...................................... 424/89; 435/237
[58] Field of Search ................. 424/89; 435/235–239

[56] References Cited

U.S. PATENT DOCUMENTS

| | | | |
|---|---|---|---|
| 3,052,606 | 9/1962 | Gieror et al. | 424/89 |
| 3,293,130 | 12/1966 | Slater et al. | 424/89 |
| 3,520,972 | 7/1970 | Smith et al. | 424/89 |
| 3,562,387 | 2/1971 | Lauerman | 424/89 |
| 3,709,782 | 1/1973 | Smith et al. | 424/89 |
| 3,892,627 | 7/1975 | Simons et al. | 424/89 |
| 3,937,812 | 2/1976 | Bittle et al. | 424/89 |
| 3,944,469 | 3/1976 | Bittle et al. | 424/89 |
| 4,031,204 | 6/1977 | Davis | 424/89 |
| 4,195,130 | 3/1980 | Hoshino et al. | 195/1.1 |

FOREIGN PATENT DOCUMENTS

| | | |
|---|---|---|
| 011864 | 6/1980 | European Pat. Off. |
| 11865 | 6/1980 | European Pat. Off. |
| 1081606 | 5/1960 | Fed. Rep. of Germany ........ 424/89 |
| 2512903 | 2/1975 | Fed. Rep. of Germany ........ 424/89 |
| 2702634 | 2/1978 | Fed. Rep. of Germany ........ 424/89 |
| 1492930 | 11/1977 | United Kingdom ................. 424/89 |

OTHER PUBLICATIONS

Gaskin, Current Vet. Ther. VI. Sm. An. Pract.: 1305–1308 (1977) R. W. Kirk, ed., W. B. Saunders Co.
Horzinek and Osterhaus, Arch. Virol. 59:1–15 (1979).
Pedersen, Am. J. Vet. Res. 37:567–572 (1976).
Hoshino and Scott, Cornell Vet. 68:411–417 (1978).
Osterhaus et al., Zentralbl. Veterinarmed. 25B(4):301 (1978).
Woods and Pedersen, Veterinary Microbiology 4:11–16 (1979).
Sherding, Feline Infectious Peritonitis 1(2), Feb. 1979 Compendium on Continuing Education 95–101.
Davis, S. K., Feline Infectious Peritonitis, Jul. 3 (1979) Literature Search 4 pages.
Buxton et al., Animal Microbiology vol. 2 (1977) Blackwell Sci. Ltd., pp. 406B–427, 711–715.

*Primary Examiner*—Shep K. Rose
*Attorney, Agent, or Firm*—Janice E. Williams; Richard D. Foggio; Alan D. Lourie

[57] ABSTRACT

The isolation, identification and in vitro propagation of feline infectious peritonitis virus and preparation of vaccines for immunization of animals of the genus Felis, family felidae therefrom are disclosed.

17 Claims, No Drawings

FELINE INFECTIOUS PERITONITIS VIRUS VACCINES

This invention relates to virus isolation and preparation of vaccines. In particular, the invention relates to the isolation and identification of feline infectious peritonitis (FIP) virus, to the in vitro propagation of FIP virus in tissue culture, to preparation of live virus vaccines containing FIP virus alone or in combination with other feline viruses and to processes for preparing and using such vaccines.

Feline infectious peritonitis (FIP) is a disease of both domestic and wild cats characterized by progressive debilitation and, in the "wet" or effusive form, a fibrinous peritoneal exudate. The virus affects most of the internal organs of the animal and, in the acute phase of the disease, is invariably fatal with a mortality rate of nearly 100% (Gaskin in "Current Veterinary Therapy VI. Small Animal Practice", R. W. Kirk, ed., W. B. Saunders Co. (1977), pgs. 1305-1308). Cases of FIP disease have been reported throughout the world. The virus itself is highly contagious, affecting kittens as well as adult cats of all ages.

The FIP virus has recently been identified as a Coronavirus by Horzinek and Osterhaus, *Arch. Virol.* 59:1 (1979), and is, thus, the first identified feline Coronavirus. Attempts to culture the FIP virus in vitro have, however, been unrewarding. Growth of the virus in cell cultures of the peritoneal exudate of infected kittens was reported by Pedersen, *Am. J. Vet. Res.* 37:567 (1976), but attempts to grow the FIP agent in primary and continuous cell line cultures were unsuccessful. Hoshino and Scott, *Cornell Veterinarian* 68:411 (1978), likewise reported unsuccessful attempts to isolate FIP virus in vitro. Those researchers also described the replication of FIP virus in organ cultures of feline small intestine. Propagation of FIP virus in suckling mouse brain was achieved by Osterhaus et al., *Zentralbl. Veterinarmed.* 25B(4):301 (1978). The mouse-adapted virus strain has been replicated in the brains of suckling rats and hamsters by Horzinek and Osterhaus, supra.

Although attempts have been made to protect cats against FIP disease by administration of inactivated crude tissue vaccines, all such attempts have failed to protect the animals (Gaskin, supra). In addition, virulent FIP virus, administered as a homogenized liver suspension, was used to vaccinate swine in a cross-protection study between FIP virus and porcine transmissible gastroenteritis (TGE) virus carried out by Woods and Pedersen, *Veterinary Microbiology*, 4:11 (1979), with inconclusive results.

One aspect of the present invention consists of safe and effective vaccines for the protection of animals belonging to the genus Felis, family *felidae* against FIP disease. A monovalent vaccine prepared from live FIP virus is preferably administered by the oral, intranasal or intraocular vaccination routes. Such vaccine preferably contains from about $10^2$ to about $10^4$ TCID$_{50}$/ml of the FIP virus with suitable carriers and/or stabilizers. Combination polyvalent vaccines containing vaccinal amounts of modified live feline viruses such as feline rhinotracheitis virus, calicivirus and/or panleukopenia virus and the FIP virus described herein are also objects of this invention and may be administered via oral, intranasal or intraocular routes. Preferably, any such vaccine will contain from about $10^2$ to about $10^4$ TCID$_{50}$/ml of the FIP virus and suitable carriers and/or stabilizers.

Yet another aspect of the present invention is the FIP virus, isolated in plaque-purified form and adapted to grow in cell cultures as described herein.

The FIP virus used to prepare the vaccines of this invention is isolated from the organs or tissues of animals infected with the virus. The organs or tissues are disaggregated into single cells or may be used as organ cultures. Growth of cells from the diseased tissue occurs with evidence of FIP virus infection, such as formation of multinucleated giant cells and/or cytopathic changes known to be typical of a Coronavirus. Supernatant fluids from such in vitro cultures contain virus which is infectious for susceptible cats when administered by the oral, nasopharyngeal, intramuscular, subcutaneous, intraperitoneal or intravenous routes.

The FIP virus grows readily in feline cells from any source, for example spleen, mesenteric lymph node or endothelial cells. The virus replicates in cells obtained directly from cat tissues and in continuous cell lines obtained originally from the feline. The virus will replicate at a temperature of about 30° C. to about 40° C., preferably from 34°–37° C., in cells growing in a multitude of growth media, such as Eagles' BME or MEM, McCoy's or Hanks' balanced salt solution plus lactalbumin, and is not affected by the type of growth medium used. Replication can be achieved in the presence of as much as 15% fetal calf serum which may also contain penicillin, streptomycin, fungazone or equivalent antibacterial or antifungal agents.

The FIP virus can also be propagated using co-cultivation techniques with cells from normal animals or feline cell lines. The cells of the infected tissue and the normal cells are mixed together at varying concentrations, preferably 50%–50%, or any proportions so desired as long as the amount of diseased cells will exceed 1.0% of the final cell preparation. The infectious virus is transferred from diseased cells to normal cells as demonstrated by formation of multinucleated cells and/or cytopathology. Infectious virus can be demonstrated in the supernatant fluid of such cultures by subsequent infection of susceptible animals or by any in vitro test system, such as routine viral titrations in cell cultures, serum neutralization tests, fluorescent antibody tests, enzyme labeled immunoabsorbent assays or other recognized in vitro methods.

After ascertaining that the virus has multiplied in the normal cell cultures, the cell cultures can be frozen and thawed one or more times and the virus in the supernatant fluid transferred to other normal cell cultures. This method can be repeated indefinitely with cultivation at from about 30° C. to about 40° C., preferably at 34°–37° C. For example, the FIP virus isolated and propagated in accordance with this invention has been serially passed on stable cell lines at least 80 times without exhibiting any changes. Virus content of the supernatant fluid increases with each serial cell passage until a maximum virus concentration is reached. Measurement of the virus content of the cell culture can be ascertained by in vitro tests as mentioned above or by infecting susceptible cats by any of the routes previously mentioned.

The FIP virus isolated and propagated in accordance with this invention was deposited with the American Type Culture Collection in Rockville, Maryland on Aug. 21, 1979 and has been assigned accession number VR-2004. It will be freely available on request upon issuance of this application, or any foreign equivalent thereof, as a patent.

DETAILED DESCRIPTION OF THE INVENTION

Isolation and Propagation of the FIP Virus

The FIP virus used to make the vaccines of the present invention was originally isolated by cultivation of cells from a disaggragated spleen aseptically removed from an FIP infected cat which had succumbed to the infection. To determine whether the virus was infectious for susceptible animals, mascerated tissue suspension and extratissue fluid was administered by intraperitoneal injection to a SPF (specific pathogen free) cat which subsequently died of typical FIP symptoms.

To propagate the FIP virus, the removed spleen was minced into pieces approximately 4–5 mm square, washed three times with Hanks' balanced salt solution and placed in a 1000 ml trypsinizing flask. Approximately 200 ml of 0.25% trypsin prepared in Hanks' balanced salt solution was added. A teflon magnet was added to the trypsinization flask and the entire flask was placed on a magnetic stirrer. The tissue fragments were stirred for 15 minutes, after which time the tissue fragments were allowed to settle and the supernatant trypsin was decanted and discarded. Another 200 ml of trypsin was added to the flask and the tissue fragments were again stirred for one hour. The cell containing supernatant fluid was then decanted under aseptic conditions and placed at 4° C. Trypsin solution was added and the procedure was repeated until all cells were removed from the tissue fragments and only organ stroma remained (about four times).

The trypsin-cell suspension was filtered through sterile gauze and then sedimented at 600 rpm approximately 600×gravity in a refrigerated Lourdes centrifuge. The resultant cell pack was washed with Hanks' balanced salt solution and resedimented. This procedure was repeated three times to eliminate traces of residual trypsin.

The packed cells were then diluted to 1 to 100 with growth medium consisting of McCoy's medium supplemented with 10% fetal calf serum and 100 units of penicillin, 500 mcg of streptomycin and 10 units of fungazone per ml. One hundred (100) ml of cell suspension was placed into a 1000 ml plastic Corning bottle and 5 ml into 60 mm Petri plates containing 5 mm×16 mm glass cover slips. The Corning bottle was incubated at 37° C. in a regular incubator and the Petri plates at 37° C. in a humidified carbon dioxide incubator.

Within 24 hours, cells attached to the surface of the bottle and Petri plates. Multiplication of the cells was allowed to proceed until a monolayer of cells covered the exposed surfaces under the medium. Versene and trypsin were then added to the bottle and the cells were detached from the bottle surface, resuspended in 200 ml of growth medium and replanted into two Corning plastic bottles and 60 mm Petri plates containing glass cover slips. The cell monolayer which had formed on the glass cover slips was stained with hematoxlyn and eosin histostains and observed on a Leitz microscope.

Multinucleated cells containing as many as 10–20 nuclei were noted in the stained cell preparations. Production of such multinucleated or giant cells is evidence of virus infection (probably formed by fusion of infected cells) and is a characteristic of all well established Coronaviridae.

The second passage of infected spleen cells produced abundant multinucleated cells on the glass slides which could be observed in unstained living cell preparations. Supernatant fluid was removed from the infected cells in the plastic bottle and, when introduced orally into susceptible SPF cats from the Norden Laboratories' cat colony, produced typical FIP disease symptoms and death.

A total of six serial culture passages was carried out with the FIP infected cells. Disease symptoms characteristic of FIP were seen in all SPF cats administered the supernatant fluid from each serial passage of the infected cell culture.

FIP virus was also isolated by co-cultivation of a serially propagable cell line with cells obtained from infected feline lymph nodes according to the following procedure:

An SPF cat from the Norden Laboratories cat colony was orally infected with virus obtained from the supernatant fluid of FIP infected cat spleen cells. When the infected cat was in extremis from infection and exhibited typical FIP symptoms, the animal was euthanitized and the mesenteric lymph nodes were aseptically removed.

The mesenteric lymph nodes were cut into pieces approximately 1 mm in size, washed three times with Hanks' balanced salt solution and then placed in a 1000 ml trypsinizing flask with 200 ml of 0.25% trypsin. A teflon covered magnet was introduced into the flask and rotation of the magnet was allowed to occur over a magnetic stirrer. Disaggregation of the cells was allowed for one hour. The fluid and cells were decanted from the tissue fragments and stored at 4° C. Fresh trypsin (200 ml) was placed on the tissue fragments. This procedure was continued until only tissue stroma remained and nearly all cells were suspended in supernatant fluid (about three times).

The trypsin-cell suspension was then sedimented at 600 rpm for 10 minutes in a refrigerated Lourdes centrifuge. The resultant cell pack was washed with Hanks' balanced salt solution and resedimented in a like manner. This procedure was repeated three times to remove residual traces of trypsin.

The cells thus obtained consisted of numerous cell types such as hematopoietic cells, epithelial cells and some unidentified cell types. These cells were suspended in Eagle's MEM (minimum essential medium) plus 10% embryonic calf serum and regular tissue culture antibiotics consisting of penicillin, streptomycin and fungizone. The lymph node cells were then mixed with a feline continuous cell line (NL-FK-1) so that enough NL-FL-1 cells were present to form a monolayer of cells in a 1000 ml plastic Corning screw cap bottle. The combined cells were allowed to incubate at 37° C. until a monolayer of cells could be microscopically observed. A 60 mm Petri plate containing glass cover slips was inoculated with 5 ml of the dual cell suspension and incubated in a humidified incubator in the presence of 5% carbon dioxide and 95% air.

When a monolayer of cells was observed (within 48 hours following infection), the glass cover slips were removed and stained with hematoxlyn-eosin. Cytopathology indicating Coronaviridae infection was observed, which is characterized by giant multinucleated cell formation, cell degeneration with retraction and detachment from the glass surface.

Supernatant fluid from the plastic bottle was removed and introduced into normal or uninfected NL- FK-1 cells. These cells were incubated at 37° C. until multinucleation of cells could be observed in an unstained or living state.

Serial cultivation of the FIP virus in the NL-FK-1 cell line was carried out. Supernatant fluid from virus passages 1 to 30 caused typical FIP clinical symptoms and death when introduced orally, intraperitoneally, intravenously, subcutaneously or intramuscularly into susceptible cats. The virus also caused a cytopathic change in the NL-FK-1 cell line resulting in destruction of the cell monolayer. The virus can be serially passed continually and indefinitely in the NL-FK-1 cell line.

Co-cultivation of FIP infected cells from other feline tissues or cultures can also be carried out.

In order to conclusively establish and identify the FIP virus as a Coronavirus, supernatant fluids from cell cultures were sedimented at 25,000×gravity for two hours, then the resultant pellet of virus was sedimented through a sucrose gradient, subjected to phosphotungstic acid staining and examined in a transmission electron microscope. The aggregate virus particles demonstrated the typical morphologic characteristics of a Coronavirus, for example infectious bronchitis virus of chickens, the prototype of the Coronaviridae. The FIP virus thus isolated was deposited in the American Type Culture Collection on Aug. 21, 1979 and given accession number VR-2004.

Preparation and Use of FIP Virus Vaccines

A live virus vaccine was prepared by diluting virulent FIP virus suspensions 1 to 100. A dose of 1.0 ml of the diluted virus suspension was administered to two susceptible cats via the oral route. Three weeks later a 1 to 50 dilution of the same material was administered to the same cats in identical manner. No disease symptoms were observed in either of the treated animals.

Subsequent dilutions of the FIP virus were made, increasing the virus concentration until each cat received 1.0 ml of a 1 to 5 dilution. No clinical symptoms of FIP were observed after the administration of each such virus dilution. Three weeks after administration of the final dilution, the cats were challenged with 1.0 ml of undiluted FIP infected tissue suspension by the oral route. Two susceptible animals were similarly infected at the same time. The unvaccinated animals exhibited classic FIP disease symptoms and died at seven and ten days post infection. The vaccinated animals remained healthy and free of any symptoms of disease.

After three weeks, the immunity of the two surviving vaccinated animals was again challenged. Two control unvaccinated cats succumbed to the disease, while the immunized animals remained healthy and free of disease symptoms. A third challenge three weeks after the second challenge and a forth challenge six months after the third resulted in the vaccinated cats remaining healthy and free of disease symptoms and all control unvaccinated animals (two per challenge) succumbing to FIP disease.

A further aspect of this invention is the preparation and use of combination vaccines consisting of vaccinal amounts of the FIP virus and one or more known feline viruses. For example, live virus feline vaccines consisting of vaccinal amounts of modified feline rhinotracheitis virus, calicivirus, and/or panleukopenia virus combined with FIP virus can be prepared for oral, intraocular or intranasal administration. Such polyvalent vaccine will, preferably, contain from about 10% to about 20 % total volume of FIP virus. An example of a polyvalent vaccine contemplated by this invention consists of from 10–20% of FIP virus, 20–30% of feline rhinotracheitis virus, 20–30% of calicivirus and 10–20% of panleukopenia virus (all percentages based on total volume).

The preparation and use of such combination vaccines is carried out according to procedures described herein or within the knowledge of those skilled in the art of vaccine production and use.

What is claimed is:

1. A live feline infectious peritonitis virus vaccine for oral, intranasal or intraocular administration capable of inducing immunity in animals of the genus Felis, family felidae without serious side effects comprising a vaccinal amount of from about $10^2$ to about $10^4$ $TCID_{50}$/ml of live feline infectious peritonitis virus which, in the undiluted state, can be demonstrated to be infectious for susceptible cats by any known in vitro method or by causing typical feline infectious peritonitis clinical disease symptoms and death when administered by the oral, nasopharyngeal, intramuscular, subcutaneous, intraperitoneal or intravenous routes and which can be serially passed on stable cell lines without exhibiting any change, and a carrier therefor.

2. The feline infectious peritonitis virus vaccine of claim 1 wherein the feline infectious peritonitis virus is isolated and propagated in cell cultures at about 30°–40° C.±2° C.

3. The feline infectious peritonitis virus vaccine of claim 2 wherein the feline infectious peritonitis virus is isolated and propagated in feline cells.

4. The feline infectious peritonitis virus vaccine of claim 3 wherein the feline infectious peritonitis virus is isolated and propagated in primary feline cells.

5. The feline infectious peritonitis virus vaccine of claim 4 wherein the feline infectious peritonitis virus is isolated and propagated in feline kidney cells.

6. The feline infectious peritonitis virus vaccine of claim 3 wherein the feline infectious peritonitis virus is passaged at least once in feline cells.

7. The feline infectious peritonitis virus vaccine of claim 5 wherein the feline infectious peritonitis virus is passaged at least once in feline kidney cells.

8. The feline infectious peritonitis virus vaccine of claim 7 wherein the feline infectious peritonitis virus is passaged from 1 to about 100 times in feline kidney cells.

9. The feline infectious peritonitis virus vaccine of claim 8 wherein the feline infectious peritonitis virus is passaged from 1 to about 30 times in feline kidney cells.

10. The feline infectious peritonitis virus vaccine of claim 1, 2, 3, 4, 5, 6, 7, 8 or 9 wherein the feline infectious peritonitis virus is ATCC No. VR-2004.

11. A method of vaccinating animals of the genus Felis, family felidae comprising administering to said animals by the oral, intranasal or intraocular route the live feline infectious peritonitis virus vaccine of claim 1 or 10.

12. A combination live virus feline vaccine for oral, intranasal or intraocular administration capable of inducing immunity in animals of the genus Felis, family felidae without serious side effects comprising a vaccinal amount of from about $10^2$ to about $10^4$ $TCID_{50}$/ml of live feline infectious peritonitis virus and vaccinal amounts of one or more vaccinal feline viruses selected from modified feline viral rhinotracheitis virus, calicivirus and panleukopenia virus, and a carrier therefor.

13. The combination vaccine of claim 12 which contains from about 10% to about 20% total volume of feline infectious peritonitis virus.

14. The combination vaccine of claim 13 which contains from 10–20% total volume of feline infectious peritonitis virus, 20–30% total volume of modified feline rhinotracheitis virus, 20–30% total volume of calicivirus and 10–20% total volume of panleukopenia virus.

15. A method of vaccinating animals of the genus Felis, family felidae comprising administering to said animals by the oral, intranasal or intraocular route a combination vaccine of claim 12, 13 or 14.

16. The combination live virus feline vaccine of claim 12 wherein the feline infectious peritonitis virus is ATCC No. VR-2004.

17. A method of vaccinating animals of the genus Felis, family felidae comprising administering to said animals by the oral, intranasal or intraocular route the combination vaccine of claim 16.

* * * * *